United States Patent
Perkins

(10) Patent No.: US 9,772,388 B2
(45) Date of Patent: Sep. 26, 2017

(54) METHOD AND SYSTEM FOR QUANTIFYING HEPATIC FAT IN HUMANS

(71) Applicant: KONINKLIJKE PHILIPS N.V., Eindhoven (NL)

(72) Inventor: Thomas Perkins, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 604 days.

(21) Appl. No.: 14/347,768

(22) PCT Filed: Sep. 28, 2012

(86) PCT No.: PCT/IB2012/055175
§ 371 (c)(1),
(2) Date: Mar. 27, 2014

(87) PCT Pub. No.: WO2013/046158
PCT Pub. Date: Apr. 4, 2013

(65) Prior Publication Data
US 2014/0232403 A1 Aug. 21, 2014

Related U.S. Application Data

(60) Provisional application No. 61/540,106, filed on Sep. 28, 2011.

(51) Int. Cl.
*G01R 33/48* (2006.01)
*G01R 33/38* (2006.01)
(Continued)

(52) U.S. Cl.
CPC .......... *G01R 33/4828* (2013.01); *A61B 5/055* (2013.01); *A61B 5/4244* (2013.01);
(Continued)

(58) Field of Classification Search
CPC G01R 33/4828; G01R 33/3808; G01R 33/50; G01R 33/383; A61B 5/055; A61B 5/4244; A61B 5/4872
See application file for complete search history.

(56) References Cited

U.S. PATENT DOCUMENTS 4,240,439 A 12/1980 Abe et al.
4,857,847 A 8/1989 Machida
(Continued)

FOREIGN PATENT DOCUMENTS

JP 2006149583 A 6/2006
WO 2010058295 A2 5/2010

OTHER PUBLICATIONS

Thomsen, C. et al "Quantification of Liver Fat using Magnetic Resonance Spectroscopy", Magnetic Resonance Imaging, vol. 12, No. 3, Jan. 1994, pp. 487-495.
(Continued)

*Primary Examiner* — Rodney Bonnette

(57) ABSTRACT

A probe unit (100) including a magnet (102, 103) generates a static magnetic $B_0$ field in an examination region and a RF coil (105). An input-output module (201) includes a transmitter (203) which controls the RF coil (105) to excite resonance and cause echoes (210) and a receiver (204) which demodulates and digitizes the echoes (210). A data processing module (206) includes at least one processor programmed to calculate a $T_2$ relaxation distribution plot from a digitized echo (210) train, calculate a first area under the fat peak on the $T_2$ distribution plot, calculate a second area under a water peak on the $T_2$ distribution plot, and normalize the first and second area to determine a fat-to-water ratio.

17 Claims, 5 Drawing Sheets

(51) Int. Cl.
*G01R 33/50* (2006.01)
*A61B 5/00* (2006.01)
*A61B 5/055* (2006.01)
*G01R 33/383* (2006.01)

(52) U.S. Cl.
CPC ........ *A61B 5/4872* (2013.01); *G01R 33/3808* (2013.01); *G01R 33/50* (2013.01); *G01R 33/383* (2013.01)

(56) References Cited

U.S. PATENT DOCUMENTS

| | | | |
|---|---|---|---|
| 5,072,732 | A | 12/1991 | Rapoport |
| 5,213,788 | A * | 5/1993 | Ranney .............. A61K 47/4823 424/617 |
| 6,091,242 | A | 7/2000 | Hanawa |
| 6,285,901 | B1 | 9/2001 | Taicher et al. |
| 6,404,197 | B1 | 6/2002 | Anderson |
| 7,564,245 | B2 | 7/2009 | Lee |
| 2003/0060697 | A1 | 3/2003 | Zhang |
| 2007/0219443 | A1 | 9/2007 | Ehnholm et al. |
| 2008/0039708 | A1 | 2/2008 | Taicher et al. |
| 2009/0167304 | A1 | 7/2009 | Prado |
| 2009/0276187 | A1 * | 11/2009 | Martin .................. G01N 24/08 702/189 |
| 2010/0068746 | A1 | 3/2010 | Nakajima |
| 2013/0158387 | A1 | 6/2013 | Tanttu |

OTHER PUBLICATIONS

Pineda, N. et al "Measurement of Hepatic Lipid: High-Speed T2-Corrected Multiecho Acquisition at 1H MR Spectroscopy—A Rapid and Accurate Technique" Radiology, vol. 252, No. 2, Jun. 2009, pp. 568-576.

Reeder, Scott B. "Quantitative Assessment of Liver Fat with Magnetic Resonance Imaging and Spectroscopy", Journal of Magnetic Resonance Imaging, vol. 34, No. 4, Sep. 2011 pp. 729-749.

Liu, C.Y. et al "Fat Quantification with IDEAL Gradient Echo Imaging: Correction of bias from T1 and Noise", Magnetic Resonance in Medicine, vol. 58, Jul. 2007 pp. 354-364.

Bydder, M. et al "Assessment of Liver Fat Quantification in the Presence of Iron", Magnetic Resonance Imaging, vol. 28, No. 6, Jul. 2010, pp. 767-776.

Kleinberg, R.L. et al "Novel NMR Apparatus for Investigating an External Sample", Journal of Magnetic Resonance, vol. 97, No. 3, May 1992, pp. 466-485.

Volke, Frank "Pocket Sized Magnetic Resonance Imaging" Science Daily, 2008.

Magritek Products, 2011.

Veliyulin, Emil et al "In Vivo Determination of Fat Content in Atlantic Salmon (Salmo Salar) with a Mobile NMR Spectrometer", Journal of the Science of Food and Agriculture, vol. 85, 2005, pp. 1299-1304.

Horch R.A. et al: Correlation of IH NMR Characteristics and Mechanical Properties in Human Cortical Bone, Proceedings of the International Society for Magnetic Resonance in Medicine, 18TH meeting and Exhibition,Stockholm, Sweden, May 1-7, 2010,vol. 18, Apr. 17, 2010 (Apr. 17, 2010), p. 541.

Bertram H C et al: "Changes in Porcine Muscle Water Characteristics during Growth-An in Vitro Low-Field NMR Relaxation Study", Journal of Magnetic Resonance, Academic Press, Orlando, FL, US, vol. 157, No. 2, Aug. 2002 (Aug. 1, 2002), pp. 267-276.

Metz H et al: Benchtop-NMR and MRI-A new analytical tool in drug Journal of Pharmaceutics,Elsevier BV, NL,vol. 364, No. 2, Dec. 2008 (Dec. 8, 2008) pp. 170-175.

Manz B et al: "A simple, small and low cost permanent magnet design to produce homogeneous magnetic fields", Journal of Magnetic Resonance, Academic Press, Orlando, FL, US, vol. 192, No. I, May 1, 2008 (May 1, 2008) pp. 131-138.

* cited by examiner

CPMG METHOD OF TRANSMITTING PHASE RECOVERY PULSES AND RECEIVING SPIN-ECHO PEAK RF SIGNALS

US 9,772,388 B2

METHOD AND SYSTEM FOR QUANTIFYING HEPATIC FAT IN HUMANS

CROSS-REFERENCE TO PRIOR APPLICATIONS

This application is the U.S. National Phase application under 35 U.S.C. §371 of International Application No. PCT/IB2012/055175, filed on Sep. 28, 2012, which claims the benefit of U.S. Provisional Patent Application No. 61/540,106, filed on Sep. 28, 2011. These applications are hereby incorporated by reference herein.

The present application relates to monitoring of hepatic fat in a subject through nuclear magnetic resonance (NMR).

Recent medical resonance imaging (MRI) studies have focused on quantifying the amount of hepatic fat in patients. Hepatic fat quantification can be used to detect Non-alcohol Fatty Liver Disease (NAFLD) and to monitor the effect of treatment of the disease. NAFLD occurs when an abnormal amount of fat is retained in the liver, the accumulation known as steatosis, for reasons not related to excessive alcohol use. If patients are left untreated, they may develop degenerative liver disease, including fibrosis, cirrhosis, and hepatocellular carcinoma.

Currently, relevant clinical information for detecting and monitoring NAFLD has been provided by MRI and the generation of fat fraction maps through the mDIXON method. Invasive biopsy procedures have also been used to detect NAFLD and monitor treatment. The main drawbacks associated with these methods are excessive cost, limited patient access, and invasiveness. At-risk patients (pre-diabetic, Type-II diabetics, obese patients, etc.) would benefit from a lower cost method to test for hepatic fat that can be easily performed in outpatient clinics or physician offices.

The present application provides a new and improved monitoring system which overcomes the above-referenced problems and others by offering a low-cost, non-invasive, and accessible solution. Similar to the apparatus employed in oil well logging systems, a portable magnet system is proposed which detects the NMR properties of an outside environment (R. L. Kleinberg et al., Novel NMR Apparatus for Investigating an External Sample, Journal of Magnetic Resonance 97, 466-485 (1992)). This system differs from the conventional NMR apparatus, wherein a sample is fit inside of a surrounding magnet and RF coil, by creating a static magnetic field along an external surface and investigating samples outside of a magnet and coil. This configuration is also known as inside-out NMR. A magnetic field of relatively low homogeneity is formed along an external surface and a small RF coil is used to perform NMR on a patient's liver. Analysis of time relaxation constants similar to that performed in table-top food analyzers allows for the amount of hepatic fat to be easily quantified.

While the use of an NMR apparatus to investigate an external sample has been substantively disclosed in the oil well logging industry, there is a need to create a low cost and accessible NMR system for detecting and monitoring the level of hepatic fat in patients.

In accordance with one aspect, a magnetic resonance system for quantifying an amount of fat in a patient is provided. The system includes a probe unit with a magnet and RF coil and a data acquisition apparatus with an input-output module and at least one processor. The magnet generates a static magnetic $B_0$ field in an examination region outside of the probe unit. The input-output module receives a RF resonance signal from the RF coil and converts it to digital data. The at least one processor analyzes the digital data signal in order to determine the amount of fat in a patient.

In accordance with another aspect, a method for quantifying an amount of fat in a patient is provided. The method includes positioning a probe unit adjacent to a region of interest to generate a static $B_0$ magnetic field, transmitting a RF excitation signal to the region of interest with a RF coil included in the probe unit to excite resonance, receiving RF signals from the region of interest, converting the resonance signals to digital MR data, and analyzing the digital MR data to calculate a fat-to-water ratio.

In accordance with another aspect, an apparatus for quantifying the amount of hepatic fat in a patient is provided. The apparatus includes a portable NMR probe and at least one processor programmed to calculate a $T_2$ relaxation distribution plot from a digitized magnetic resonance echo signal, calculate a first area under a hepatic fat peak and a second area under a water peak located on the $T_2$ relaxation distribution plot, and normalize the first and second area to generate a hepatic fat-to-water ratio.

One advantage resides in providing a low-cost system for quantifying hepatic fat.

Another advantage, particularly for at-risk patients, is that hepatic fat monitoring can be performed in outpatient clinics or physician offices.

Another advantage resides in visually depicting the quantity of hepatic fat and a fat-to-water ratio for a patient on a display.

Yet another advantage resides in quickly providing diagnostic information to a patient regarding their liver environment, such as the likelihood of an overabundance of iron or degenerative liver diseases.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 1:
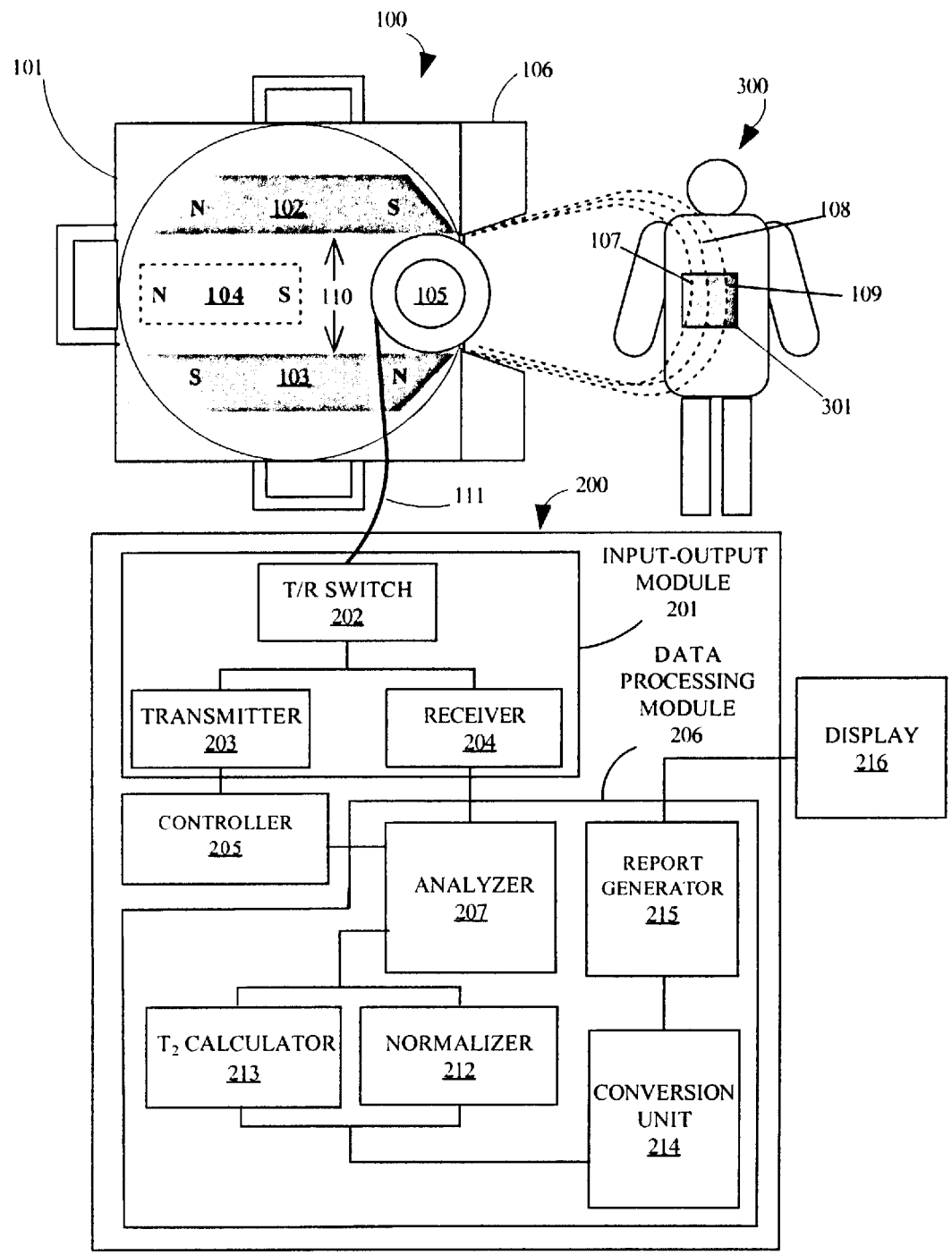
FIG. 1 is a schematic diagram and functional block diagram of a system for quantifying an amount of hepatic fat in a patient according to one embodiment of the present application.

With reference to FIG. 1, a portable NMR probe 100 performs low-field, time domain nuclear magnetic resonance (TD-NMR) inside of target tissue, e.g. a liver, of a patient 300 in a region defined as the sensitive zone 301. A static $B_0$ magnetic field is generated by two or more magnet pieces 102 and 103 of opposite polarity that are mounted in a biocompatible base or housing portion 101. This $B_0$ magnetic field aligns the spin states of hydrogen nuclei found within the sensitize zone 301. A suitable material for magnets includes samarium cobalt, niobium, other rare earth magnets, electromagnets, and the like. However, other magnetic materials are contemplated as are known to those having ordinary skill of the art. The biocompatible base portion is preferably positioned above the lower right lobe of a patient's liver. In one embodiment, the magnets are configured such that within 5 cm of the magnet pieces 102 and 103, the static magnetic field lines extend transversely with approximately 100 ppm homogeneity and the sensitive zone 301 is a few centimeters. This region of relative field homogeneity is where NMR data is most easily and accurately acquired.

The location of the region of magnetic homogeneity is controlled, in one embodiment, by the geometry of the magnet pieces 102 and 103. Increasing a gap distance 110 between the magnet pieces 102 and 103 decreases the depth of the homogenous field region in the sensitive zone 301, while reducing the gap increases the depth. In another embodiment, an additional magnet piece 104 is movably disposed between the two magnet pieces 102 and 103 to alter the depth of the homogenous field region. By way of example, magnetic field lines of increasing depth in the sensitive zone are indicated as 107, 108, and 109.

The magnetic field can also be focused with the use of a passive or active focus element 106 disposed between the magnets and the sensitive zone. This element can take on a variety of shapes and sizes, including a fixed, telescoping, or adjustable annular ring. The focus element 106 contracts to narrow the magnetic field and expands to broaden the magnetic field.

Handles or a piston grip for a handheld embodiment or mounting structures for a robotically supported embodiment also extend from the biocompatible base or housing 101 for positioning of the portable NMR probe 100 to create the static $B_0$ magnetic field in the sensitive zone 301, e.g. contacting the patient's skin over the liver region to be examined.

The portable NMR probe 100 also includes an RF coil 105, which is placed in a cavity between the two magnet pieces 102 and 103. The RF coil 105 can be of varying sizes and configurations. The RF coil 105 is preferably made of a high-conductivity material that maximizes a signal-to-noise ratio. The RF coil 105 in one embodiment includes two current opposed loops which produce an RF or $B_1$ field perpendicular to a face of the coil. The RF coil 105 in another embodiment is a figure-eight shaped coil. Other coil configurations include single loop coils, coil arrays, focused coils, directional coils, quadrature coils, the like are also contemplated. Separate transmit and receive coils of different configurations are also contemplated.

The RF frequency of the RF coil 105 is adjustable to the Larmor frequency at the $B_0$ field strength of selectable depths such as 107, 108, and 109. With continuing reference to FIG. 1 and further reference to FIG. 2, a transmitter 203 of an input output module controls the RF coil 105 to generate an RF excitation pulse 208, e.g. a 90° pulse, at the Larmor frequency, to form an excitation field or pulse perpendicular to the $B_0$ static magnetic field. The Larmor frequency ($f_L$) in this application is defined as $f_L=\lambda_H B_0$, where $\lambda_H$ is a gyromagnetic ratio for hydrogen (42.57 Mhz/T) and $B_0$ the strength of the static $B_0$ magnetic field. Because the gyromagnetic ratio of hydrogen varies with how the hydrogen is bound to other atoms, the RF frequency is typically a spectrum that spans resonance frequencies of the target tissues. This RF excitation pulse 208 excites (tips) the hydrogen nuclei within the sensitive region 301 and causes them to precess around the axis of the $B_0$ magnetic field with the Larmor frequency. The transmitter 203 also controls the RF coil 105 to generate 180° inversion pulses 209 to reverse the precession and cause magnetic resonance echoes. The RF coil 105 also receives resonance RF signals, particularly echoes 210 from the nuclei excited to resonance.

Over time, the resonance signal looses energy as the magnetization precesses back into alignment with the $B_0$ field at a rate 211 which is proportional to $1/T_2$ relaxation time. Since the $T_2$ relaxation times differ for the hydrogen in fats, bound water, free water and other chemical bonding states, NMR can differentiate between molecules such as lipids and water. Lipids have a greater electron density than water and the resonance signal from lipids decays faster than the resonance signal from water, i.e. the $T_2$ of lipids is shorter than the $T_2$ of water.

Figure 2:
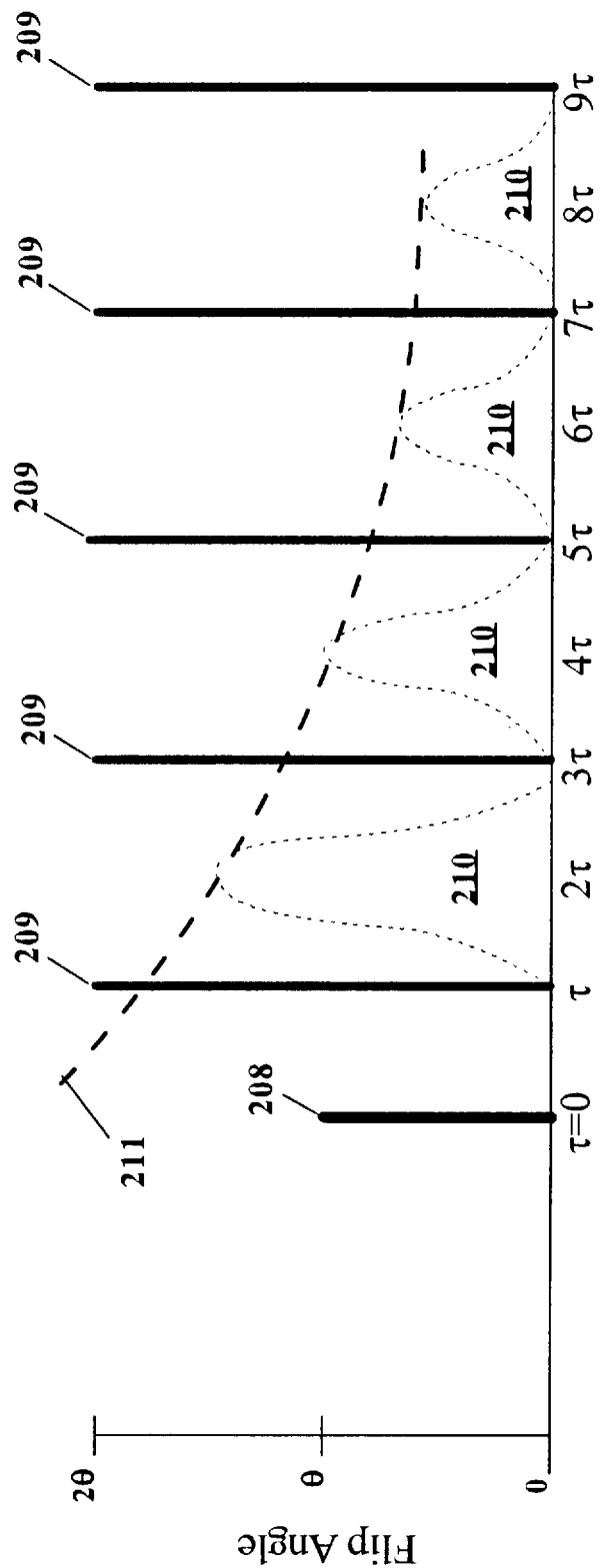
FIG. 2 is graph which illustrates a Carr-Purcell-Meiboom-Gill (CPMG) spin echo technique implemented by one embodiment of the system of FIG. 1.

The input-output module 201 includes a transmit/receive switch 202, the transmitter 203, and a receiver 204. The transmit/receive switch 202 connects either one of the transmitter or the receiver to the RF coil 105. The transmitter 203 is typical of those found in modern MRI devices, including the ability to modulate a digital signal input to an output RF signal. The receiver 204 is also typical of those found in modern MRI devices, including the ability to demodulate, amplify, and digitize a received RF resonance echo signal. The transmitter 203 is connected to a controller 205 which controls the transmitter 203 to transmit a selected magnetic resonance sequence at a frequency that excites and manipulates resonance in the magnetic field at a selected depth. For example, the controller causes the transmitter 203 to transmit a Carr-Purcell-Meiboom-Gill (CPMG) sequence to excite resonance and manipulate the resonance to create the series of echoes 210. As illustrated in FIG. 2, the CPMG sequence includes a excitation pulse 208, such as a 90° pulse, to excite resonance and a series of 180° inversion pulses 209 to repeatedly refocus the magnetization into the series of echoes 210.

With particular reference to FIG. 2, the RF excitation pulse 208 transmitted from the RF coil 105 excites an exponentially decaying resonance signal 211. As the resonance signal decays, hydrogen nuclei return to their equilibrium state through various relaxation processes. Their precession frequency is dependent upon the local magnetic field strength $B_0$. Due to the different resonance (Larmor) frequencies of the hydrogen in different chemical bonding states, homogeneity variations in the static $B_0$ magnetic field, and the like, hydrogen nuclei magnetization dephases over time as it decays. The inversion pulses 209 flip the magnetization 180° causing the magnetization vector components of the various resonance frequencies to start rephasing. Although the CPMG pulse sequence is illustrated, other sequences, such as Pulse Field Gradient Spin-Echo (PF-GSE), Carr-Purcell (CP), or the like are also contemplated.

The multi-exponential rate of decay 211 of spin-echo peaks 210 is characterized by the $T_2$ relaxation time, also known as the spin-spin relaxation time. The decaying resonance signal includes a train of the spin-echo peaks 210 which occur between phase recovery inversion pulses 209. The series of echoes 210 generated by the CPMG sequence get progressively smaller as the excited resonance decays.

A data acquisition unit 200 is built into or connected to the portable NMR probe 100. The data acquisition unit 200 is controlled by the controller 205 to apply pulse sequence radiofrequencies to a patient 300, perform data acquisition, and process data to generate qualitative measurements of fat and water in the sensitive zone 301. A data processing unit 206 receives the echo signals 212 from the receiver 204. Because the $H^1$ dipole in free water, bound water (e.g. liver tissue), and lipid (e.g. hepatic fat) resonates at characteristically different but close frequencies, each signal is a composite of free water, bound water, and lipid signals. Each signal measured can be represented by a sum of exponentials, as shown in Eqn. 1 below, in which the overall multi-exponential rate of decay 211 contains contributions from the decay of free water, bound water, and lipid.

$$S(t)=\Sigma_0^{T2\,max} A\exp(-t/T2) \qquad (1)$$

S is the signal measured by the receiver 203 at time t, which is proportional to the total number of $H^1$ dipoles resonating at time t. A represents amplitude of the signal. The summation is performed from $T_2$=0 ms to $T_2$ max, which is the longest value of $T_2$ on the end of the CPMG sequence. There will be separate terms in equation (1) for free water, bound water, and lipid. Referring to FIG. 2, signal readings at a number of time points corresponding the spin echo peaks 210 (e.g. 2t, 4t, 6t, 8t) are used to solve equation (1) for $T_2$.

Figure 3:
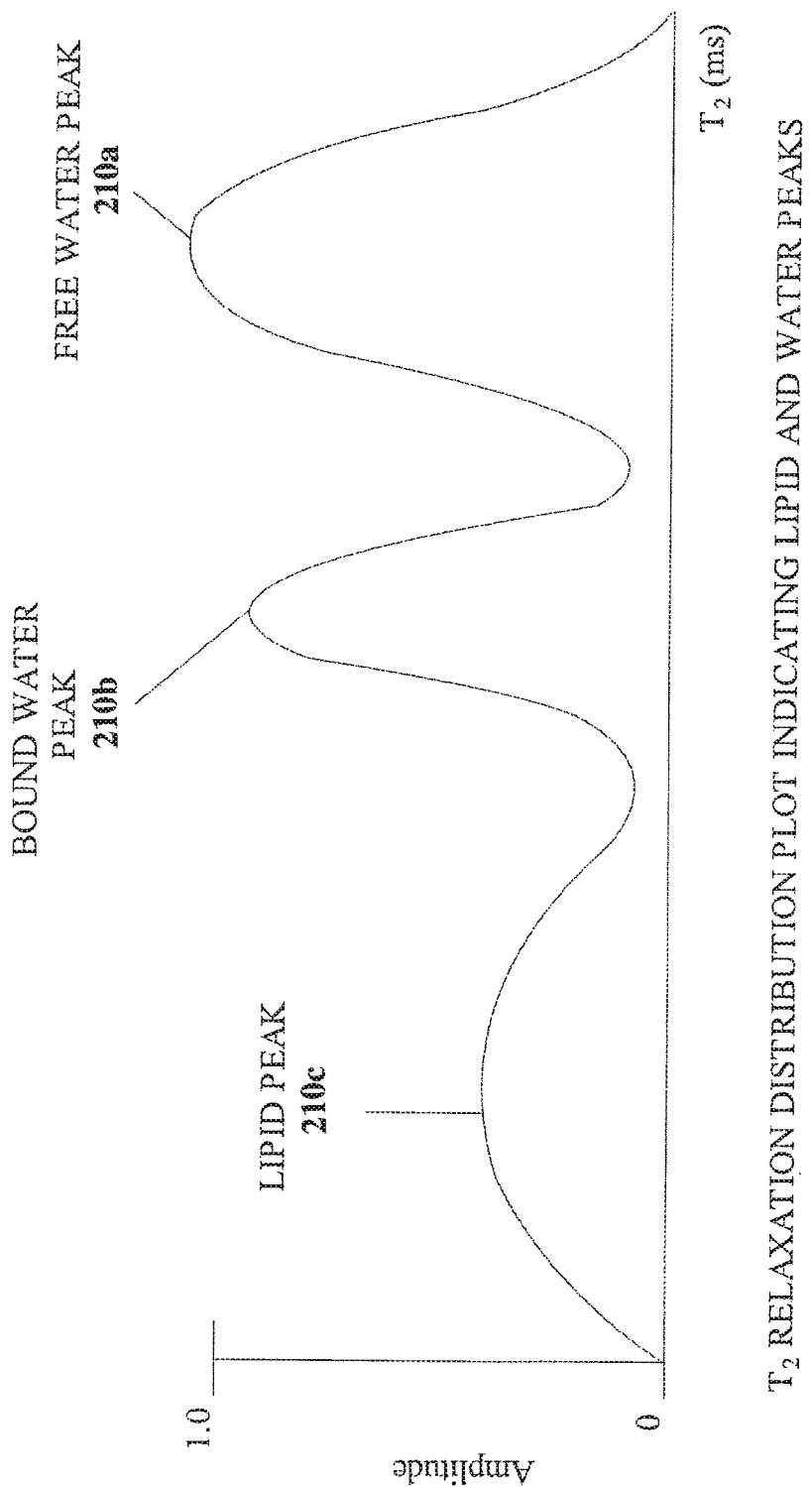
FIG. 3 is a graph which illustrates a $T_2$ relaxation distribution plot illustrating hepatic fat, bound water, and free water peaks.

An analyzer unit or module 207 uses a fitting technique to calculate the inversion of multi-exponential equation (1) and determine a $T_2$ relaxation distribution, which is represented graphically in FIG. 3. For example, the analyzer unit 207 applies a transform to the string of echoes 210 from the frequency domain, e.g. a Fourier Transform. Fitting techniques include smoothing methods, singular value decompositions (SVD), solid iteration rebuild techniques (SIRT), and those other methods commonly employed to solve a linear inversion problem. The analyzer plots a $T_2$ relaxation distribution graph similar to that seen in FIG. 3, which shows a separation of the signal from the spin echoes 210 into a free water peak 210a, bound water peak 210b, and a lipid peak 210c.

With containing reference to FIG. 3, the lipid $T_2$ peak 210c has a shorter $T_2$ relaxation time relative to water due to the increased electron density around hydrogen nuclei in lipids compared to water. Bound water has an increased electron density relative to free water, and therefore has a longer $T_2$ than lipid and shorter $T_2$ than pure water. Bound water and free water may occur in partially overlapping peaks.

A normalizing unit 212 calculates the area under the lipid peak and divides it by the area under the corresponding water peaks to generate a normalized lipid value, e.g. percent lipid. In a healthy liver region, the lipid (hepatic fat) value will be very small. The lipid value is displayed on a display device 216, e.g. a video monitor, printer, or the like and/or saved to memory. A diagnostician uses this lipid value to diagnose fatty liver diseases.

The echoes contain other diagnostic information. As previously mentioned, the $T_2$ relaxation time is inversely proportional to a rate of decay of the peaks of the echoes 210. A $T_2$ calculating unit 213 calculates a mean $T_2$ relaxation time value for the water peaks, particularly the bound water peaks. The mean $T_2$ relaxation times are represented by the peak value of free water peak 210a, bound water peak 210b, and lipid peak 210c in the $T_2$ relaxation time distribution plot. The more iron (Fe) in the liver tissue, the faster the rate of decay and the shorter $T_2$ of the bound water. A conversion unit or module 214, such as a look up table, converts the calculated mean $T_2$ relaxation time into a level of iron which is displayed on a display unit 216 and/or saved to memory.

The $T_2$ relaxation time is also indicative of other properties of the liver or other anatomical regions. Trapped fluids increase the $T_2$ relaxation time. The $T_2$ calculating unit 212 calculates the mean $T_2$ relaxation time and the conversion unit 214 converts it to meaningful values indicative of the amount of trapped fluid for display on the display 216 and/or saving to memory.

Other changes in the liver structure also change the $T_2$ relaxation time. For example, fibrosis, cirrhosis, and other conditions which stiffen the liver, shorten the $T_2$ relaxation time for both water and lipid. The $T_2$ calculation unit 212 calculates the $T_2$ relaxation times for both the water and lipid peaks and the conversion unit 214 converts the $T_2$ relaxation times for appropriate stiffness units for display and/or storing.

In one embodiment, a computer analysis system such as a common computer based diagnosis recommendation system analyzes the $T_2$ relaxation times of various components in the body along with other available information to generate a proposed diagnosis which is displayed on the display unit 216.

In another embodiment, the analyzer unit or module 207 separates the received echo peak signal into a free water peak, bound water peak, and a lipid peak in the frequency domain by applying a Fourier Transform. The analyzer unit 207 includes fast Fourier transform (FFT) algorithms, discrete Fourier transform (DFT) algorithms, or the like. A frequency spectrum plot is generated similar to those of NMR spectrometers, in which hepatic fat peaks have a lower resonance frequency relative to free water and bound water. The area under the lipid peaks is divided by the area under the water peaks to normalize the data. Standard frequency spectrum plots representative of different conditions of the liver or other anatomical regions are located in the conversion unit 214, which compares measured frequency spectrum plots with the standard frequency spectrum plots to generate a value indicative of clinical information related to the condition(s). This value is displayed on a display unit and/or saved to memory.

In another embodiment, the data-acquisition device 206 interacts with at least an auxiliary magnet to increase the strength of the $B_0$ static magnetic field within the sensitive zone 301 and increase resolution of the frequency spectrum plot. This auxiliary magnet includes a robotic swing arm magnet, cancelling magnets or other the like. The auxiliary magnet would is positioned in such a way as to decrease leakage of the magnetic field generated in the sensitive zone 301.

The entire system indicated in FIG. 1. is expected to cost approximately \$30,000 (€ 20,000) with approximate dimensions of no larger than 10×40 cm. Even fat fraction determinations that have an absolute error of <10% still provide relevant clinical value. In addition, by virtue of the low field and the sampling method used, no room RF shielding should be necessary, making the installation of the system relatively simple within a physician's office or outpatient clinic.

The above described units and modules may include individual units such as application-specific integrated circuits (ASICs) or processors, program routines of one or more processors programmed to perform the above and below discussed steps, or the like.

In another embodiment, the output of the analyzer unit 207 is sent to the conversion unit 214, which includes a lookup table. The lookup table includes constants for lipid and water, including molecular size and weight. The lookup table also includes verified experimental data indicating how $T_2$ values shift in the presence of an overabundance of iron, cystic lesions, or degenerate liver diseases such as fibrosis, cirrhosis, and heptacellular carcinoma. The conversion unit 214 compares the calculated data output from the analyzer 207 in order to formulate diagnostic information. A report generator 214 decides which information to output and a display format for the display unit 216, e.g. a video monitor, printer, or the like and/or saved to memory. This information is preferably a diagnostic report which indicates the likelihood of liver abnormalities. The diagnostic report indicates at least hepatic fat fraction information for review by a physician or other operator.

Figure 4:
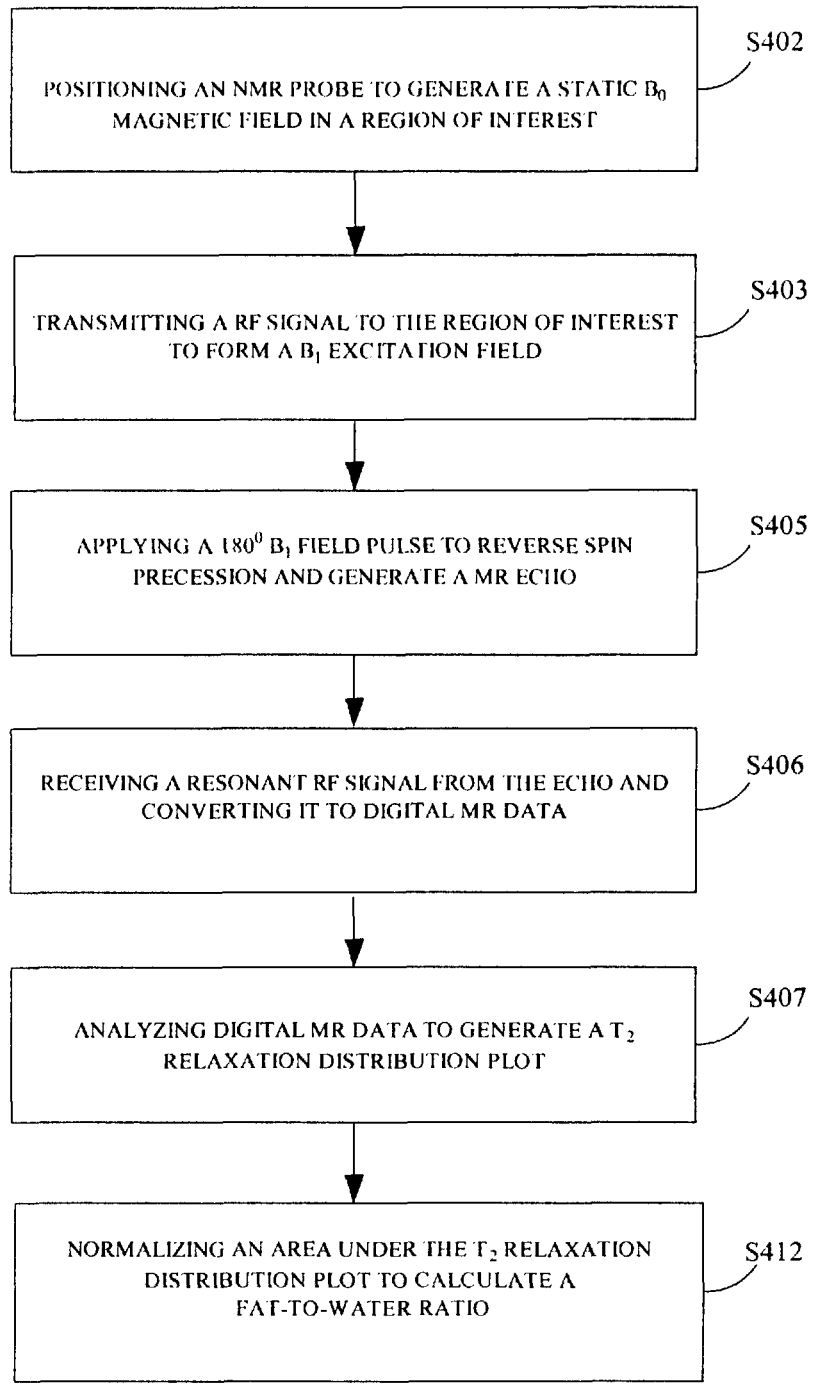
FIG. 4 is a flow diagram of a method of quantifying the amount of fat in a patient according to another embodiment of the present application.

With reference to FIG. 4, a method for quantifying an amount of fat in a subject begins at a step S402, in which the NMR probe 100 is positioned such that its static $B_0$ magnetic field is established in a region of interest 301. This region of interest 301, in the hepatic fat embodiment, includes a few cm region of magnetic field homogeneity that is ideally located in the lower right lobe of the liver. The homogenous magnetic field region is located at a selected depth within the region of interest based on probe position or adjusting magnetic field geometry, magnetic field focus, or the like. Generation of a uniform static $B_0$ magnetic field causes the spin-states of hydrogen dipoles within the region of interest to preferentially align in either a parallel or anti-parallel orientation. However, $B_0$ fields with known inhomogeneities are also contemplated.

At S403, a modulated RF signal is transmitted to the region of interest 301 to form a $B_1$ excitation field. The modulated signal originates as a digital signal sent by the transmitter 203 under control of the data processing unit 206 to the RF coil 105 for transmission to the examination region. A $B_1$ excitation field pulse 208 causes hydrogen nuclei to precess around the $B_0$ field at the Larmor frequency. At S405, a 180° $B_1$ field inversion pulse 209 is applied to reverse the precession and causes the magnetic resonance echo 210. In the CPMG sequence, the 180° pulses are applied periodically to generate the series of echoes 210 illustrated in FIG. 4. At S406, the induced magnetic resonance signal is picked up by the coil 105 and converted to digital MR data by the receiver 204.

At S407, the digital MR data is sent to the analyzer 207 from the receiver 204 and analyzed to produce a $T_2$ relaxation distribution plot. The analysis includes inversion of the summation of a multi-exponential decay 211, the summation shown in equation (1), which can be performed by common algorithms for solving an inversion problem. The $T_2$ relaxation time distribution plots amplitude against $T_2$ relaxation time similar to FIG. 3. Separation of a free water peak 210a, bound water peak 210b, and lipid peak 210c is noticeable from the plot.

At S412, an area under the respective peaks of the $T_2$ relaxation distribution plot is normalized to produce a fat-to-water ratio. To calculate the fat-to-water ratio, the normalizing unit 212 calculates the area under the lipid peak and divides it by the area under the corresponding water peaks to generate a normalized lipid value, e.g. a fat-to-water ratio or percent lipid.

Figure 5:
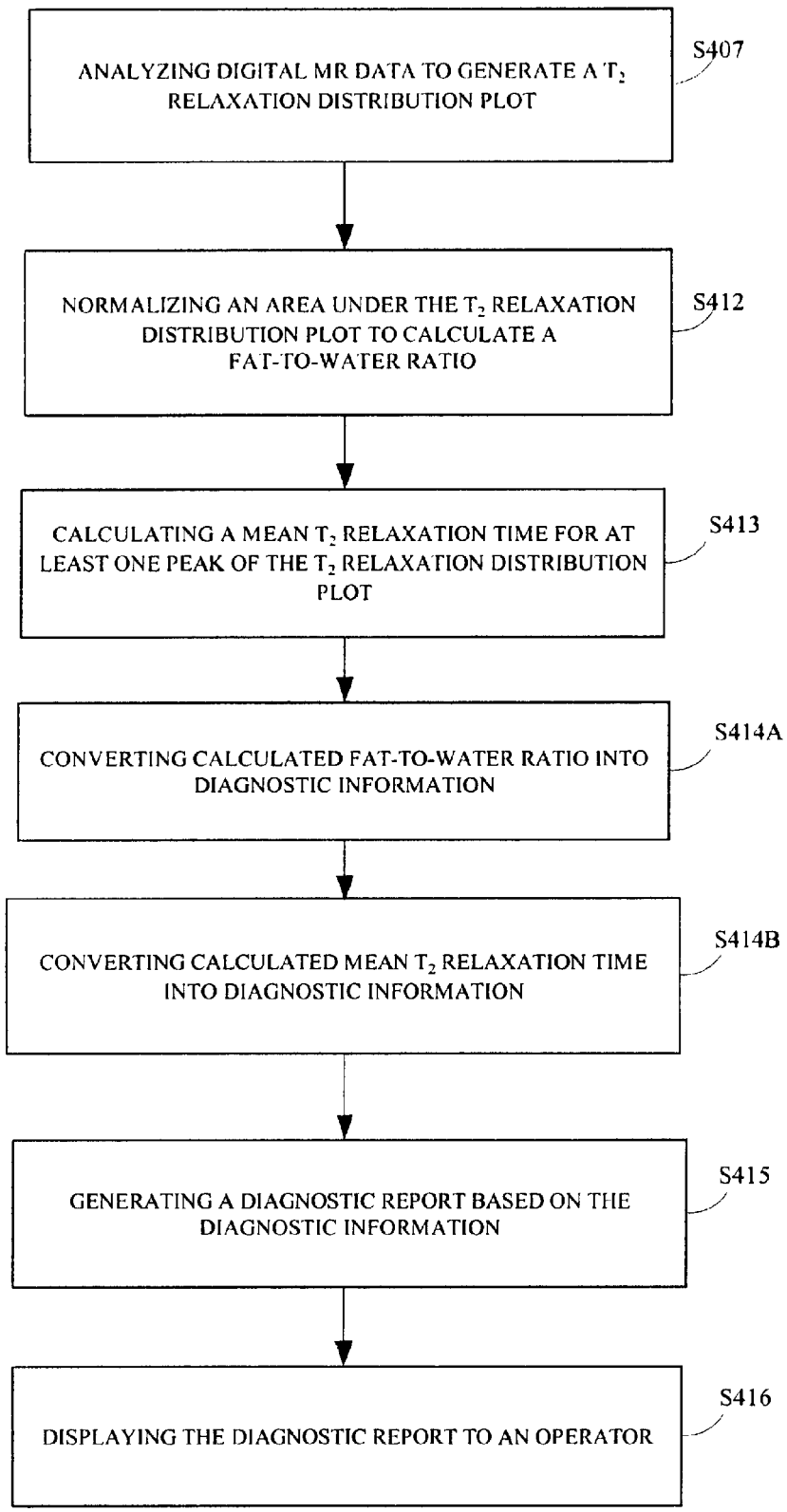
FIG. 5 is a flow diagram which illustrates the method in FIG. 4 in accordance with another embodiment of the present application.

With reference to FIG. 5, another embodiment of a method of quantifying the amount of fat in a patient is contemplated. At step S407 a $T_2$ relaxation distribution plot is generated based on analysis of digital MR data. At S412, the area under the $T_2$ relaxation distribution plot is normalized to calculate a fat-to-water ratio. At S413, a mean $T_2$ relaxation time is calculated for each of the constituent peaks in the $T_2$ relaxation distribution plot. At S414A, the calculated fat-to-water ratio is correlated with pre-determined information on the conversion unit 214, such as a lookup table, to generate diagnostic information about a patient. The pre-determined information can include common fat-to-water ratios for different anatomical conditions. Information relevant for the region of interest being examined would be used by the conversion unit 214 to generate diagnostic information.

At S414B, the calculated mean $T_2$ relaxation time from S413 is correlated with pre-determined information stored on the conversion unit 214, such as a lookup table, to generate diagnostic information. The conversion unit 214 includes verified experimental data predicting upward and downward shifts in $T_2$ corresponding to different environmental conditions of the liver. By means of example, a substantial decrease in $T_2$ for bound water indicates an abundance of iron in the liver. A slight decrease in $T_2$ for bound water, which is a noticeably smaller decrease than realized for an overabundance of iron, would indicate degenerative liver disease such as fibrosis, cirrhosis, and heptacellular carcinoma.

At S415, a diagnostic report is generated which includes a variety of diagnostic information, such as a calculated fat-to-water ratio or other diagnostic information. The diagnostic report may include just a fat-to-water ratio, or the diagnostic information generated at S414A and/or S414B. With a comprehensive lookup table, the diagnosis of particular anatomical conditions would become increasing accurate as more diagnostic readings are taken. In one embodiment, a diagnostic report generated by the report generator 215 is displayed on a display 216, e.g. a monitor or printer. The diagnostic report includes the percent likelihood of different liver conditions based on $T_2$ changes. To increase accuracy of the diagnosis, information derived from the shifting of calculated mean $T_2$ values may be combined with information derived from calculated fat-to-water ratios.

At S416, the diagnostic report generated at S415 is viewed by a physician or operator to recommend further treatment for a subject and stored in a medical records database.

It should also be appreciated that while water and lipid generally have somewhat similar $T_2$ relaxation constants, the difference is more pronounced in the liver. This increases the diagnostic value of the present application of TD-NMR in the liver. A normal amount of iron in the liver environment has also been shown to not affect results.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A magnetic resonance system for quantifying an amount of fat in a region of interest in a patient, comprising:
    a portable magnetic resonance apparatus positionable adjacent the patient, the magnetic resonance apparatus including:
        a housing configured to contact the patient's skin over the region of interest to be examined;
        a magnet disposed in the housing and configured to generate a static magnetic $B_0$ field in an examination region outside of the magnetic resonance apparatus and in the region of interest when the housing is in contact with the patient's skin; and
        an RF coil disposed in the magnetic resonance apparatus adjacent to the region of interest;
    a data acquisition apparatus connected to the RF coil, the data acquisition apparatus including:

an input-output module which receives a RF resonance signal from the RF coil and converts it to a digital signal; and
at least one processor which analyzes the digital signal from the input-output unit to determine the amount of fat in the patient, the at least one processor programmed to:
  transmit a RF signal to the region of interest to form a B1 excitation field;
  apply a 180° inversion pulse to generate a magnetic resonance echo;
  receive a resonance RF signal from the echo and converting it to digital MR data;
  analyze the digital MR data and calculate a $T_2$ relaxation distribution plot having a free water peak, a bround water peak, and a lipid peak,
  determine an area under each of the free water peak, the bound water peak, and the lipid peak in the $T_2$ relaxation distribution plot,
  normalize the area under each of the free water peak, the bound water peak, and the lipid peak,
  calculate a fat-to-water ratio from the normalized areas under the free water peak, the bound water peak, and the lipid peak.

2. The system according to claim 1, wherein the region of interest is a right lobe of a liver of the patient.

3. The system according to claim 1, wherein the at least one processor is further programmed to:
  convert the calculated fat-to-water ratio and a calculated mean $T_2$ relaxation time into diagnostic information.

4. The system according to claim 3, wherein the at least one processor is further programmed to perform at least one of:
  determining whether a patient has an overabundance of iron; and
  determining whether a patient has an anatomical disease.

5. The system according to claim 1, wherein the at least one processor sends a digital signal to an input-output module to move the static magnetic $B_0$ field.

6. The system according to claim 5, wherein the magnet includes two pole pieces separated by a changeable distance to move the static magnetic $B_0$ field further from and closer to the magnetic resonance apparatus, wherein the input-output module is configured to change the distance between the two pole pieces to move the $B_0$ field further from and closer to the magnetic resonance apparatus.

7. The system according to claim 5, wherein the magnet includes:
  two oppositely disposed pole pieces; and
  a movably mounted extra piece, wherein the input-output module is configured to move the extra piece in response to the signal from the at least one processor to move the $B_0$ field further from and closer to the magnetic resonance apparatus.

8. A method for quantifying an amount of fat in a region of interest in a patient, comprising:
  positioning a housing of a portable magnetic resonance apparatus contacting skin of the patient over the region of interest of the patient and generating a static $B_0$ magnetic field exterior to the housing in the region of interest with a magnet mounted in the housing;
  transmitting an RF excitation signal into the region of interest with an RF coil disposed in the housing of the magnetic resonance apparatus to excite resonance in the region of interest;
  applying a 180° inversion RF pulse to generate magnetic resonance echo signals from the region of interest;
  receiving the magnetic resonance echo signals from the region of interest;
  converting the magnetic resonance echo signals to digital MR data; and
  analyzing the digital MR data to calculate a fat-to-water ratio, including:
    analyzing digital MR data to generate a $T_2$ relaxation distribution plot, including a free water peak, a bound water peak, and a lipid peak,
    normalizing areas under the free water peak, the bound water peak, and the lipid peak of the $T_2$ relaxation distribution plot, and
    calculating a fat-to-water ratio based on the normalized areas.

9. The method according to claim 8, wherein the region of interest is a right lobe of the liver.

10. The method according to claim 8, further including:
  calculating a mean $T_2$ relaxation time for at least one peak of the $T_2$ relaxation distribution plot; and
  converting the calculated fat-to-water ratio and the calculated mean $T_2$ relaxation time into diagnostic information.

11. The method according to claim 10, further including at least one of:
  determining whether a patient has an overabundance of iron;
  determining whether a patient has an anatomical disease.

12. The method of claim 8, further including:
  Fourier transforming the digital ME data to generate the $T_2$ relaxation distribution plot.

13. The method according to claim 8, further including:
  adjusting the region of interest by moving the static $B_0$ magnetic field further from and closer to the probe unit.

14. The method according to claim 13, wherein the magnet includes first and second oppositely disposed pole pieces and a movably mounted piece movably mounted at least partially between the first and second pole pieces, and wherein the method further includes:
  moving the third piece to move the static $B_0$ magnetic field further from and closer to the housing.

15. A lion-transitory computer readable memory which carries computer code which controls one or more processors to perform the method according to claim 8.

16. The method according to claim 8, wherein the magnet includes first and second pole pieces, wherein the method further includes changing a distance between the first and second pole pieces to move the static $B_0$ field further from and closer to the probe unit.

17. An apparatus for quantifying a amount of hepatic fat in a region of interest in a subject, comprising:
  a portable NMR apparatus including a housing, a magnet disposed in the housing, the magnet being configured to generate a static magnetic $B_0$ field in a region of interest and an RF coil configured to generate magnetic resonance excitation signals, 180° magnetic resonance inversion signals, and receive magnetic resonance echo signals from the region of interest;
  at least one processor programmed to:
    calculate a $T_2$ relaxation distribution plot from the magnetic resonance echo signals received from the region of interest;
    calculate a first area under a hepatic fat peak of the $T_2$ relaxation distribution plot;
    calculate a second area under a water peak of the $T_2$ relaxation distribution plot;
    normalize the first and second areas; and calculate a hepatic fat-to-water ratio based on the normalized first and second areas.

* * * * *